(12) United States Patent
Goetz et al.

(10) Patent No.: US 7,526,341 B2
(45) Date of Patent: Apr. 28, 2009

(54) AMPLITUDE RAMPING OF WAVEFORMS GENERATED BY AN IMPLANTABLE MEDICAL DEVICE

(75) Inventors: Steven M. Goetz, Brooklyn Center, MN (US); Jordan A. Barnhorst, Little Canada, MN (US); James M. Hartmann, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 419 days.

(21) Appl. No.: 10/099,438

(22) Filed: Mar. 15, 2002

(65) Prior Publication Data

US 2005/0004628 A1    Jan. 6, 2005

(51) Int. Cl.
*A61N 1/08* (2006.01)
(52) U.S. Cl. .................. 607/59; 607/30; 607/45; 607/46
(58) Field of Classification Search .............. 607/1–2, 607/30–32, 39–43, 46, 59–60, 28
See application file for complete search history.

(56) References Cited

U.S. PATENT DOCUMENTS

| | | | | |
|---|---|---|---|---|
| 4,520,825 A | * | 6/1985 | Thompson et al. | 607/59 |
| 4,878,497 A | * | 11/1989 | Callaghan et al. | 607/28 |
| RE33,420 E | * | 11/1990 | Sussman et al. | 607/46 |
| 5,003,975 A | | 4/1991 | Hafelfinger et al. | |
| 5,186,170 A | * | 2/1993 | Varrichio et al. | 607/45 |
| 5,507,786 A | | 4/1996 | Morgan et al. | |
| 5,534,018 A | | 7/1996 | Wahlstrand et al. | |
| 5,626,620 A | | 5/1997 | Kieval et al. | |
| 5,741,311 A | | 4/1998 | McVenes et al. | |
| 5,755,742 A | | 5/1998 | Schuelke et al. | |
| 5,792,204 A | * | 8/1998 | Snell | 607/32 |
| RE35,987 E | * | 12/1998 | Harris et al. | 607/63 |
| 5,855,594 A | | 1/1999 | Olive et al. | |
| 5,891,179 A | | 4/1999 | Er et al. | |

(Continued)

FOREIGN PATENT DOCUMENTS

WO    WO 99/65568    12/1999

OTHER PUBLICATIONS

International Search Report for PCT/US03/06892 mailed Aug. 4, 2003.

(Continued)

*Primary Examiner*—Carl H Layno
*Assistant Examiner*—Eugene T Wu
(74) *Attorney, Agent, or Firm*—John W. Albrecht; Medtronic, Inc.

(57) ABSTRACT

The present invention automates the adjustment of an amplitude of stimulated pulses that are generated by an implanted device. Apparatus comprises a processor that communicates with the implanted device over a communications channel through a communications module. The apparatus enables the clinician to select a pair of electrodes that is contained on a lead of the implanted device. Corresponding to each iteration of the process, the processor sends a command to the implanted device in order to increment the amplitude of the stimulation pulse between the selected electrodes. Each iteration of the process corresponds to the apparatus incrementing the current value by a predetermined incremental value that can be selected by the clinician. When the current value of the amplitude equals the target value, the process is halted. Additionally, the clinician can halt process during the execution of the process by instructing the apparatus.

9 Claims, 6 Drawing Sheets

U.S. PATENT DOCUMENTS

| | | | | |
|---|---|---|---|---|
| 5,935,078 A | * | 8/1999 | Feierbach | 600/509 |
| 5,938,690 A | * | 8/1999 | Law et al. | 607/46 |
| 6,044,301 A | | 3/2000 | Hartlaub et al. | |
| 6,208,894 B1 | | 3/2001 | Schulman et al. | |
| 6,308,102 B1 | * | 10/2001 | Sieracki et al. | 607/59 |
| 6,516,227 B1 | | 2/2003 | Meadows et al. | |
| 6,738,668 B1 | * | 5/2004 | Mouchawar et al. | 607/28 |
| 6,792,310 B1 | * | 9/2004 | Turcott et al. | 607/27 |
| 2001/0037132 A1 | | 11/2001 | Whitehurst et al. | |

OTHER PUBLICATIONS

European Examination Report, Communication pursuant to Article 943 EPC, for European patent application No. 03 726 035.3-2310, dated Nov. 3, 2008, 3 pages.

* cited by examiner

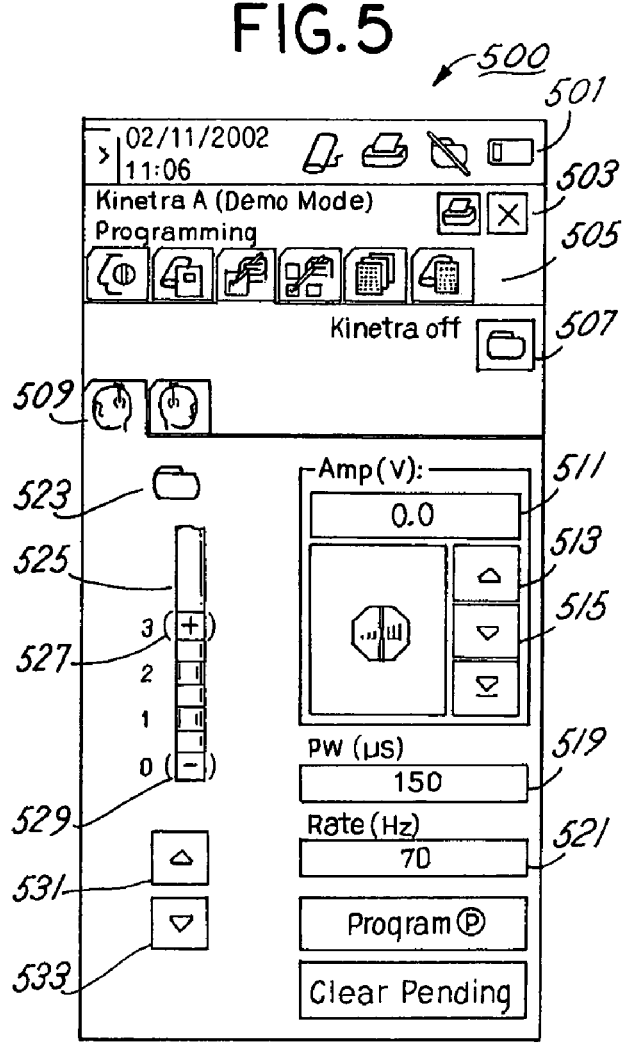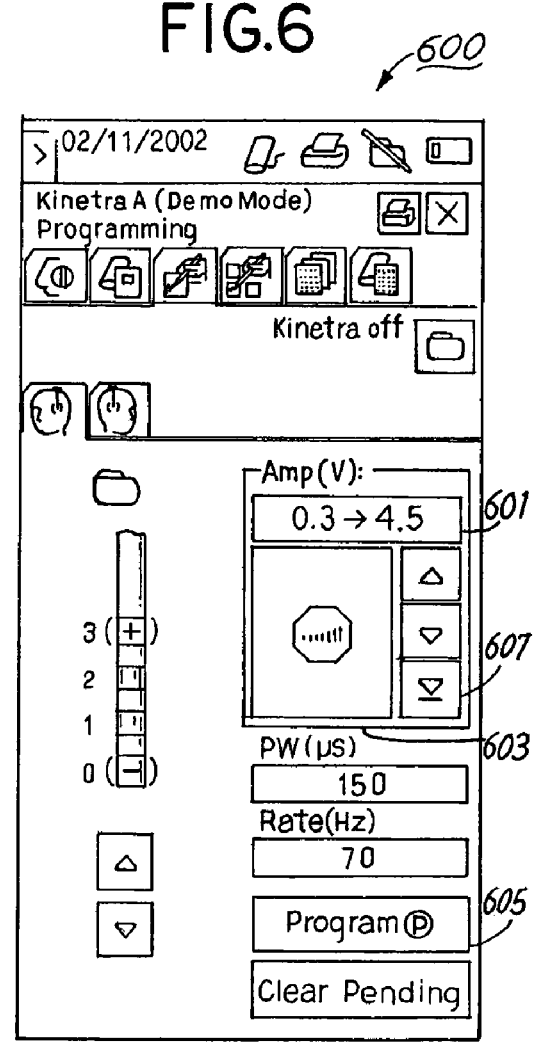

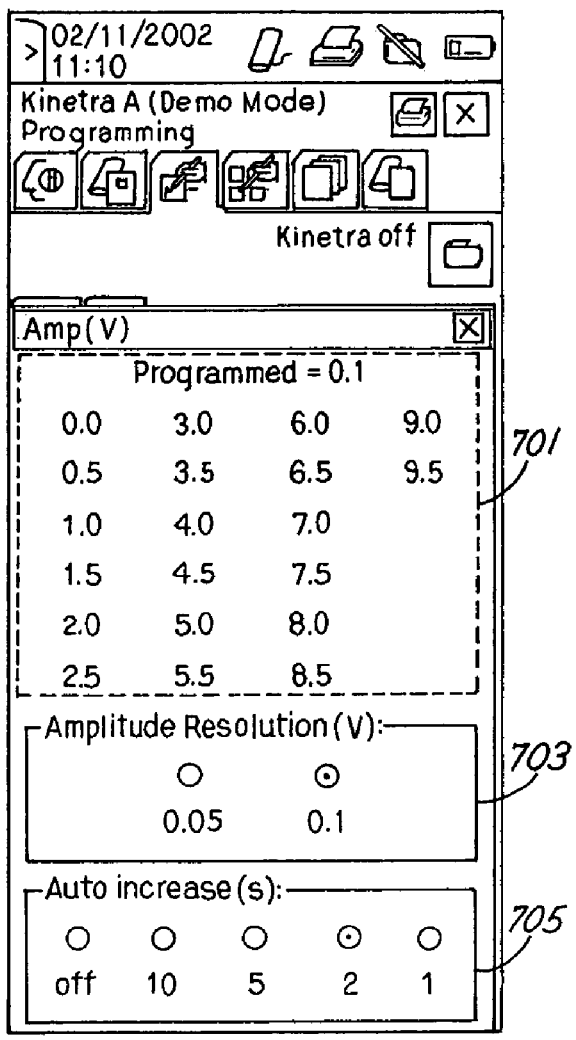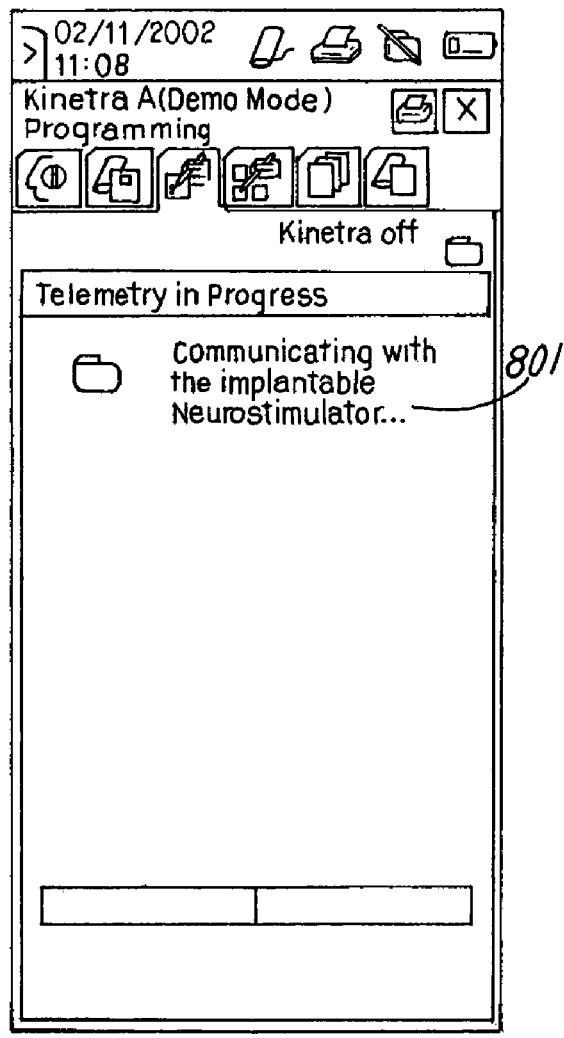

AMPLITUDE RAMPING OF WAVEFORMS GENERATED BY AN IMPLANTABLE MEDICAL DEVICE

RELATED APPLICATION

This disclosure is related to the following co-pending application entitled "AUTOMATED IMPEDANCE MEASUREMENT" by inventor Goetz, et al., having U.S. patent application Ser. No. 10/099,436 and filed on Mar. 15, 2002, which is not admitted as prior art with respect to the present disclosure by its mention in this section.

FIELD OF THE INVENTION

This invention relates generally to implantable medical devices, and more particularly to the adjustment of the amplitude of a waveform generated by implantable medical devices.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

One type of implantable medical device is an Implantable Neuro Stimulator (INS). The INS delivers mild electrical impulses to neural tissue using an electrical lead. The neurostimulation targets desired neural tissue to treat the ailment of concern. For example, in the case of pain, electrical impulses (which are felt as tingling) may be directed to cover the specific sites where the patient is feeling pain. Neurostimulation can give patients effective pain relief and can reduce or eliminate the need for repeat surgeries and the need for pain medications.

Implantable medical devices such as neurostimulation systems may be partially implantable where a battery source is worn outside the patient's body. This system requires a coil and/or an antenna to be placed on the patient's skin over the site of the receiver to provide energy and/or control to the implanted device. Typically, the medical device is totally implantable where the battery is part of the implanted device. The physician and patient may control the implanted system using an external programmer. Such totally implantable systems include, for example, the Itrel® 3 brand neurostimulator sold by Medtronic, Inc. of Minneapolis, Minn.

In the case of an INS, for example, the system generally includes an implantable neurostimulator (INS) (also known as an implantable pulse generator (IPG)), external programmer(s), and electrical lead(s). The INS is typically implanted near the abdomen of the patient. The lead is a small medical wire with special insulation. It is implanted next to the spinal cord through a needle and contains a set of electrodes (small electrical contacts) through which electrical stimulation is delivered to the spinal cord. The lead is coupled to the INS via an implanted extension cable. The INS can be powered by an internal source such as a battery or by an external source such as a radio frequency transmitter. The INS contains electronics to send precise, electrical pulses to the spinal cord, brain, or neural tissue to provide the desired treatment therapy. The external programmer is a hand-held device that allows the physician or patient to optimize the stimulation therapy delivered by the INS. The external programmer communicates with the INS using radio waves.

Traditionally, clinicians determine the optimum therapy settings for a particular patient through a process of iterative trial and error. In an interactive session with the patient, the voltage amplitude of the stimulation pulses is increased and decreased (titrated) until a range of settings is found that proves efficacious for the patient's symptoms. This process is similarly applied in both the pain therapy and the movement disorder (MvD) therapies, with the key difference being in the feedback time period. With pain, the patient can usually provide feedback immediately; in MvD, the symptoms change more slowly.

With previous programmers, the process of iterating through a set of amplitude values involved many discrete programmings. Each programming typically involves multiple keystrokes, making the whole process tedious and often too slow for the patient and the physician.

BRIEF SUMMARY OF THE INVENTION

In a first embodiment, a voltage amplitude of stimulated pulses that are generated by an implanted device is incrementally adjusted. The embodiment utilizes apparatus and methods to automate an associated process, thus facilitating the process for the clinician. The apparatus comprises a processor that communicates with the implanted device over a communications channel through a communications module. In the embodiment, the communications channel is a telemetry channel. The apparatus enables the clinician to select at least a pair of electrodes that is contained on a lead of the implanted device. The embodiment supports a user interface in which the clinician inputs information through a touch-sensitive screen. Corresponding to each iteration of the process, the processor sends a command to the implanted device in order to increment the amplitude of the stimulation pulse between the selected electrodes. The implanted device sends a response on the telemetry channel in the reverse direction to verify the execution of the command. Each iteration of the process corresponds to the apparatus incrementing the current value by a predetermined incremental value that can be selected by the clinician. When the current value of the amplitude equals the target value, the process is halted. Additionally, the clinician can halt process during the execution of the process by instructing the apparatus. The embodiment enables the clinician to select other specified parameters, e.g. pulse width and pulse rate, that are associated with stimulation pulses.

Alternative embodiments can incrementally adjust other specified parameters that are associated with the stimulation pulses. Moreover, alternative embodiments can support a user interface that is physically separate from a programmer and a user interface that utilizes other modes of inputting information such as a keypad or a voice recognition capability.

BRIEF DESCRIPTION OF THE DRAWINGS

FIG. 5 shows a programming tab with amplitude ramp control screen that is displayed on a user interface;

FIG. 6 shows a ramp in progress screen that is displayed on a user interface;

FIG. 7 shows an amplitude and ramp time step selection screen that is displayed on a user interface; and FIG. 8 shows a completing a ramp screen that is displayed in a user interface.

DETAILED DESCRIPTION OF THE INVENTION

Figure 1:
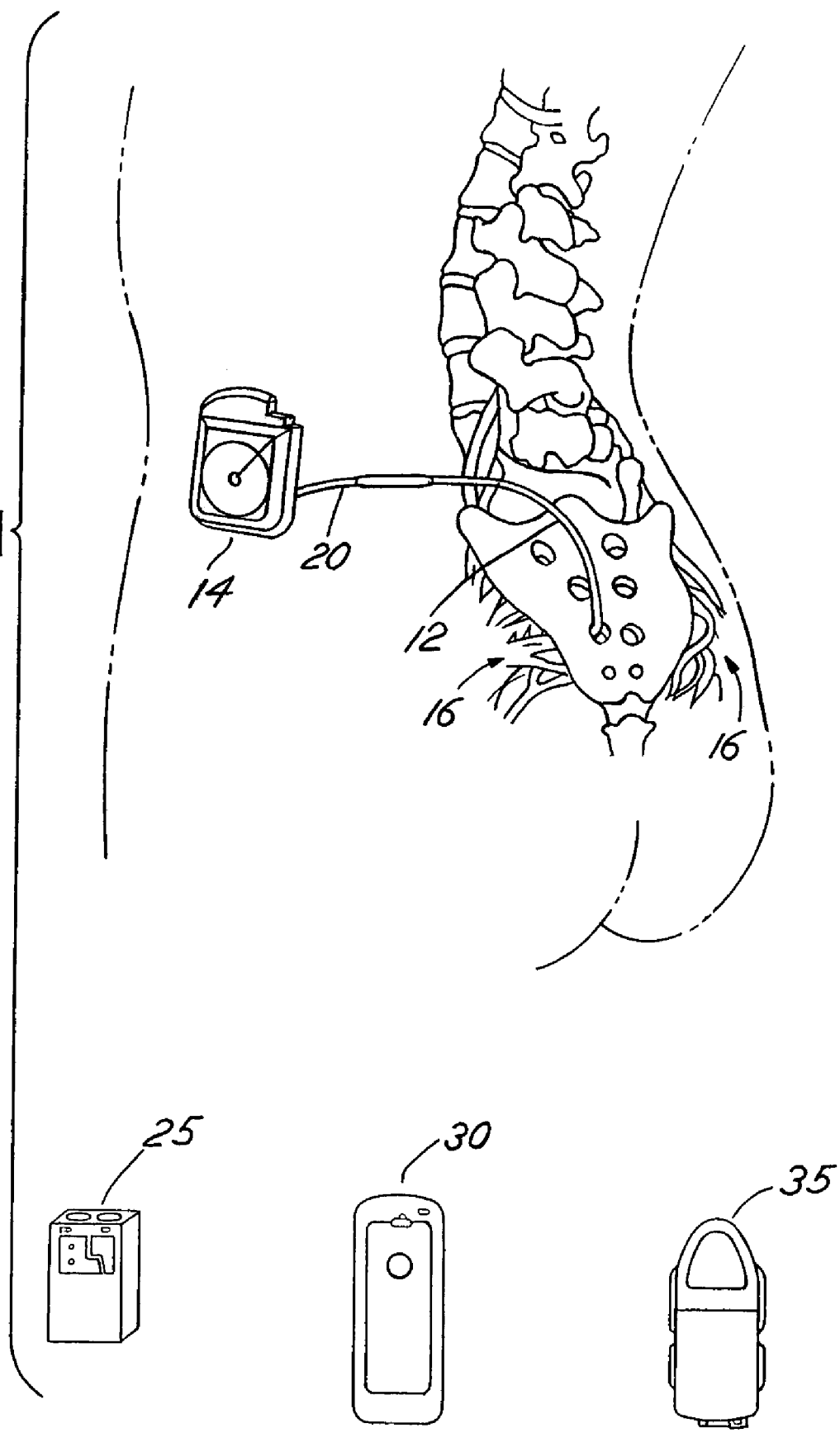
FIG. 1 illustrates an implantable medical device in accordance with a preferred embodiment of the present invention, as implanted in a human body.

FIG. 1 shows the general environment of an Implantable Neuro Stimulator (INS) medical device 14 in accordance with a preferred embodiment of the present invention. The neurostimulation system generally includes an INS 14, a lead 12, a lead extension 20, an External Neuro Stimulator (ENS) 25, a physician programmer 30, and a patient programmer 35. The INS 14 preferably is a modified implantable pulse generator that will be available from Medtronic, Inc. with provisions for multiple pulses occurring either simultaneously or with one pulse shifted in time with respect to the other, and having independently varying amplitudes and pulse widths. The INS 14 contains a power source and electronics to send precise, electrical pulses to the spinal cord, brain, or neural tissue to provide the desired treatment therapy. In the embodiment, INS 14 provides electrical stimulation by way of pulses although alternative embodiments may use other forms of stimulation such as continuous electrical stimulation.

The lead 12 is a small medical wire with special insulation. The lead 12 includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 12 may also be a paddle having a plurality of electrodes including, for example, a Medtronic paddle having model number 3587A. In yet another embodiment, the lead 12 may provide electrical stimulation as well as drug infusion. Those skilled in the art will appreciate that any variety of leads may be used to practice the present invention.

The lead 12 is implanted and positioned to stimulate a specific site in a spinal cord 16 or the brain. Alternatively, the lead 12 may be positioned along a peripheral nerve or adjacent neural tissue ganglia like the sympathetic chain or it may be positioned to stimulate muscle tissue. The lead 12 contains one or more electrodes (small electrical contacts) through which electrical stimulation is delivered from the INS 14 to the targeted neural tissue. If the spinal cord is to be stimulated, the lead 12 may have electrodes that are epidural, intrathecal or placed into the spinal cord itself. Effective spinal cord stimulation may be achieved by any of these lead placements.

Although the lead connector can be connected directly to the INS 14, typically the lead connector is connected to a lead extension 20 which can be either temporary for use with an ENS 25 or permanent for use with an INS 14. An example of the lead extension 20 is Model 7495 available from Medtronic.

The ENS 25 functions similarly to the INS 14 but is not designed for implantation. The ENS 25 is used to test the efficacy of stimulation therapy for the patient before the INS 14 is surgically implanted. An example of an ENS 25 is a Model 3625 Screener available from Medtronic.

The physician programmer 30, also known as a console programmer, uses telemetry to communicate with the implanted INS 14, so a physician can program and manage a patient's therapy stored in the INS 14 and troubleshoot the patient's INS system. An example of a physician programmer 30 is a Model 7432 Console Programmer available from Medtronic. The patient programmer 35 also uses telemetry to communicate with the INS 14, so the patient can manage some aspects of her therapy as defined by the physician. An example of a patient programmer 35 is a Model 7434 Itrel® 3 EZ Patient Programmer available from Medtronic.

Those skilled in the art will appreciate that any number of external programmers, leads, lead extensions, and INSs may be used to practice the present invention.

Implantation of an Implantable Neuro Stimulator (INS) typically begins with implantation of at least one stimulation lead 12 usually while the patient is under a local anesthetic. The lead 12 can either be percutaneously or surgically implanted. Once the lead 12 has been implanted and positioned, the lead's distal end is typically anchored into position to minimize movement of the lead 12 after implantation. The lead's proximal end can be configured to connect to a lead extension 20. If a trial screening period is desired, the temporary lead extension 20 can be connected to a percutaneous extension with a proximal end that is external to the body and configured to connect to an External Neuro Stimulator (ENS) 25. During the screening period the ENS 25 is programmed with a therapy and the therapy is often modified to optimize the therapy for the patient. Once screening has been completed and efficacy has been established or if screening is not desired, the lead's proximal end or the lead extension proximal end is connected to the INS 14. The INS 14 is programmed with a therapy and then implanted in the body typically in a subcutaneous pocket at a site selected after considering physician and patient preferences. The INS 14 is implanted subcutaneously in a human body and is typically implanted near the abdomen of the patient.

Figure 2A:
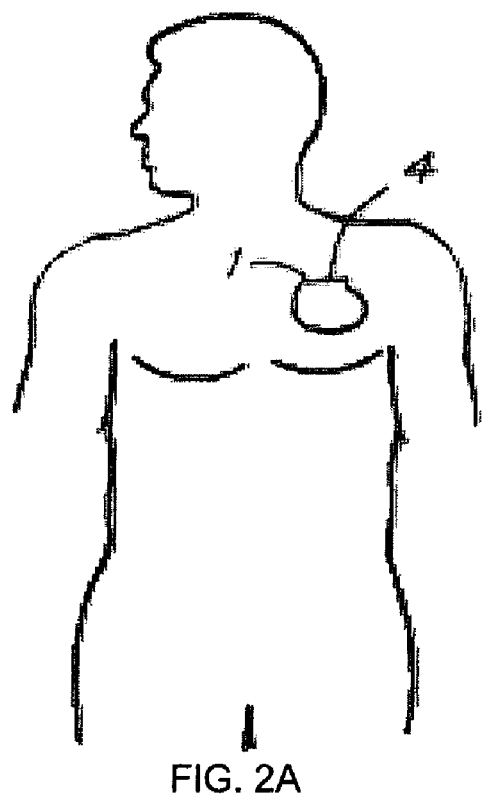
FIGS. 2A-D illustrates locations where the implantable medical device of the present invention can be implanted in the human body other than the location shown in FIG. 1.
Figure 2B:
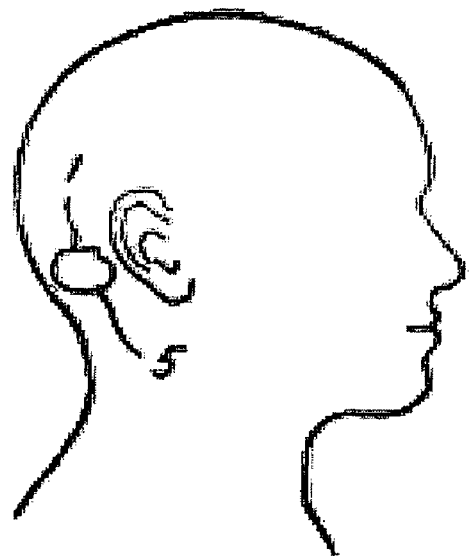
Figure 2C:
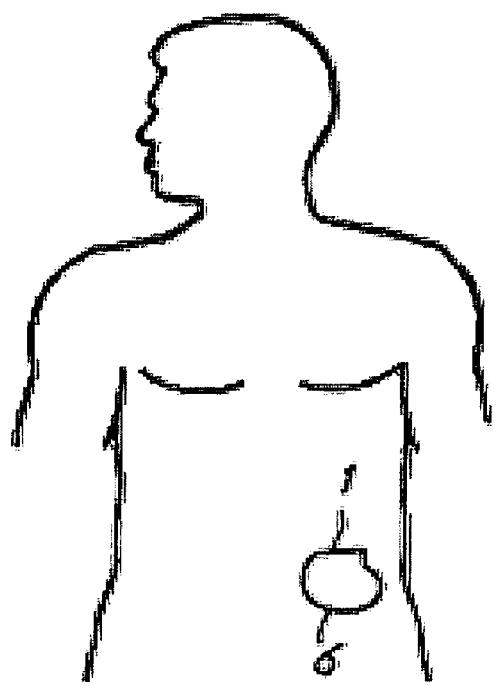
Figure 2D:
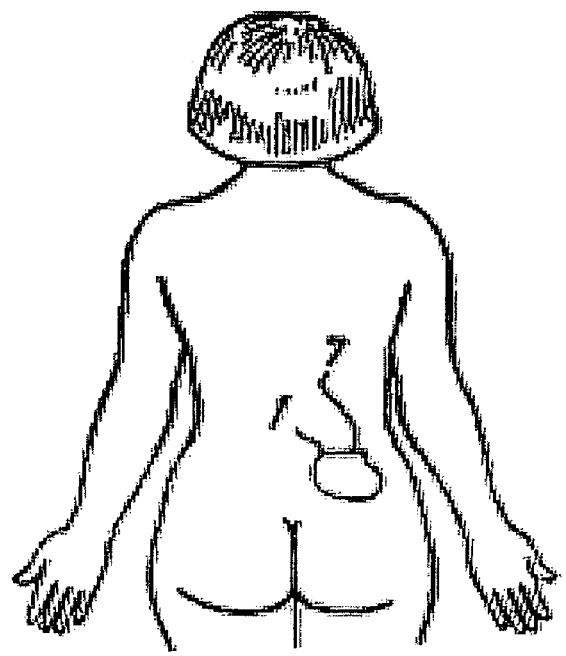

The above embodiment for the placement of the INS 14 within the lower left abdominal region 6 of the patient is further illustrated in FIG. 2C. Other preferred embodiments for the placement of stimulator 1 within a human patient is further shown in FIGS. 2A, 2B, and 2D. As shown in FIG. 2A, the INS 14 can be implanted in a pectoral region 4 of the patient. As shown in FIG. 2B, the INS 14 can be implanted in a region 5 behind the ear of a patient, and more specifically in the mastoid region. As shown in FIG. 2D, the INS 14 can be placed in the lower back or upper buttock region 7 of the patient. The INS 14 is discussed in further detail herein.

The physician periodically uses the physician programmer 30 to communicate with the implanted INS 14 to manage the patient therapy and collect INS data. The patient uses the patient programmer 35 to communicate with the implanted INS 14 to make therapy adjustment that have been programmed by the physician, recharge the INS power source, and record diary entries about the effectiveness of the therapy. Both the physician programmer 30 and patient programmer 35 have an antenna or coil locator that indicates when the telemetry head is aligned closely enough with the implanted INS 14 for adequate telemetry.

Optionally, the neurostimulation system may include a sensor to provide closed-loop feedback control of the INS 14. For example, the INS 14 may receive feedback instructions from an external component, which processes a recorded signal from the sensor and sends instruction to signal generator via antenna.

Figure 3:
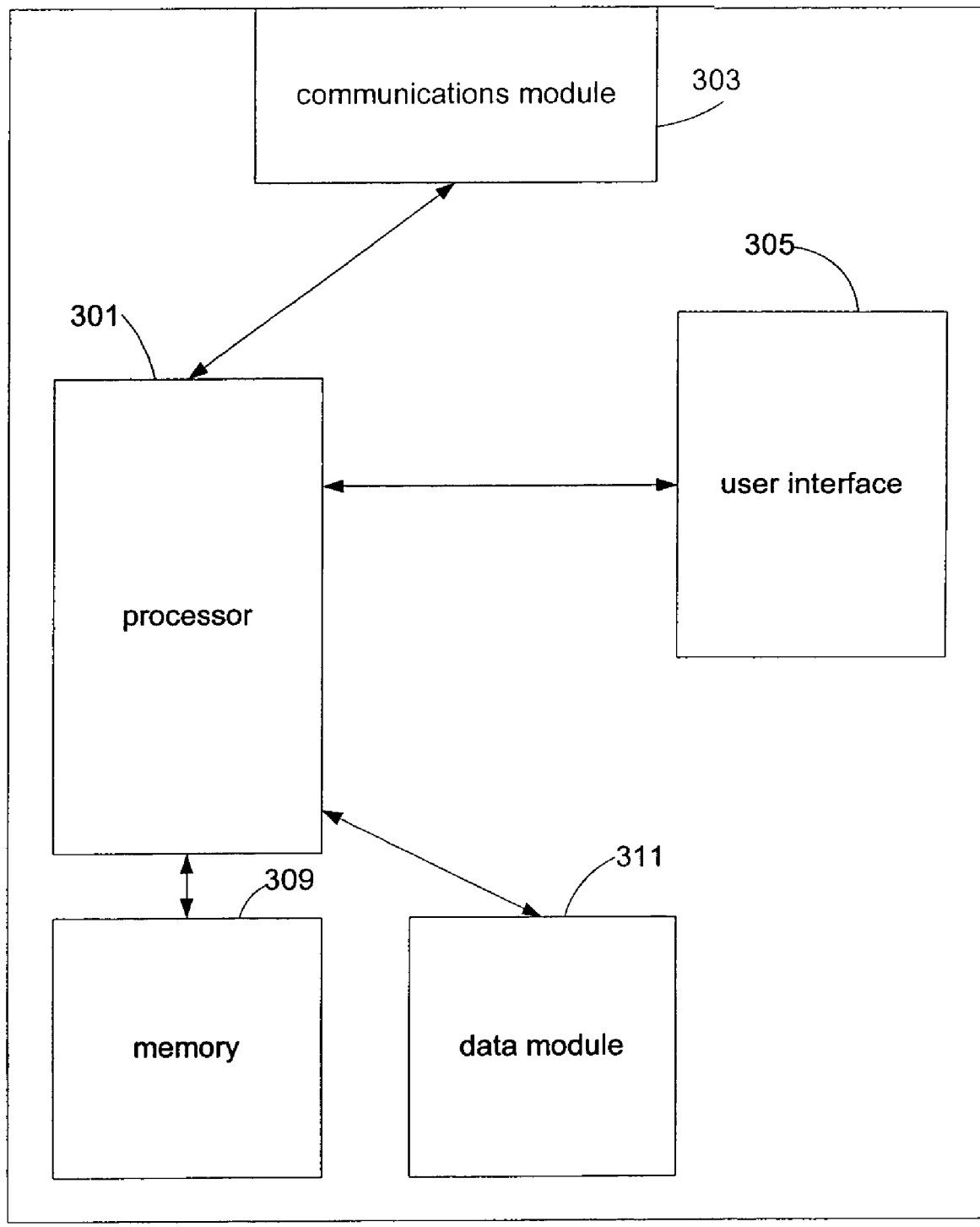
FIG. 3 shows an architecture of a programmer in accordance with an embodiment.

FIG. 3 shows an architecture of the programmer 30 in accordance with an embodiment of the present invention. A processor 301 communicates to the INS 14 through a communications module 303 over a radio channel. With alternative embodiments, the communications module 303 can correspond to other types of communications channels, including an infrared (IR) channel and a cabled channel. In the embodiment, the communications module 303 provides communications from the processor 301 to the INS 14 and from the INS 14 to the processor 301 (i.e. two-way communications.) Thus, the processor 301 can command the INS 14 to perform an action, and the INS 14 can consequently return a response to the processor 301. The processor 301 displays information to a user and receives responses and commands from the user, e.g. a clinician, through a user interface 305. The programmer 30 comprises the user interface 305 in the embodiment. The clinician inputs information and commands through a touch-sensitive screen, although an alternative embodiment can utilize other input devices such as a keyboard or can utilize a voice recognition capability to identify inputs articulated by the clinician. Also, an alternative embodiment can implement the user interface 305 that is external to processor, e.g. with a laptop computer through a data port. In another alternative embodiment, the processor 301 stores the impedance measurements in a memory 309 for later retrieval by the clinician. The processor 301 executes computer instructions that are contained in the memory 309. Patient data, e.g. parameter settings of the INS 14 is contained in a data module 311, which is a pluggable memory device. However, an alternative embodiment can store patient data in the memory 309 utilizing a data structure.

Figure 4:
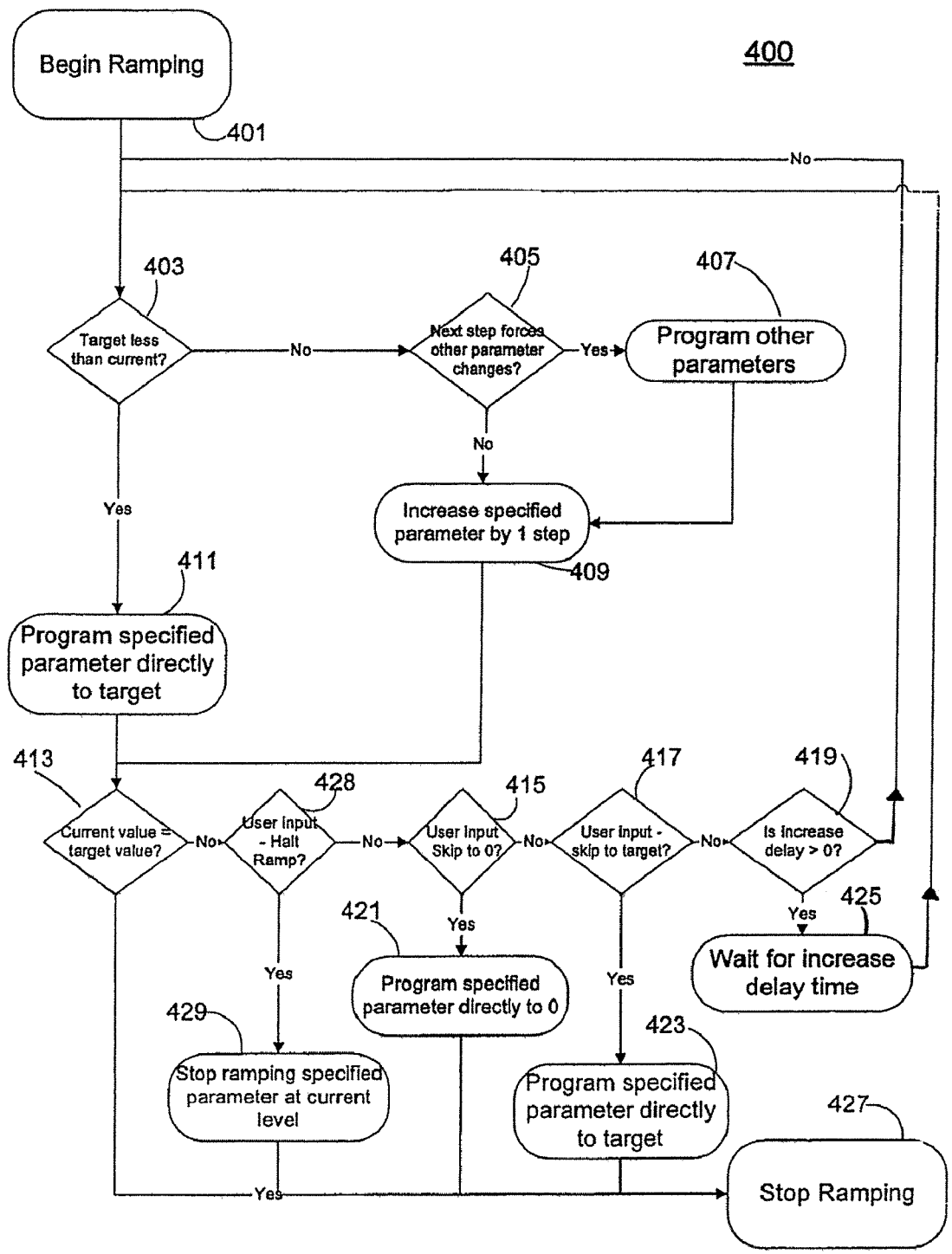
FIG. 4 shows a flow diagram for ramping the amplitude of stimulation pulses according to an embodiment of the present invention.

FIG. 4 shows a flow diagram for ramping the amplitude of stimulation pulses between a pair of electrodes according to an embodiment of the present invention. The processor 301 through the communications module 303 instructs the INS 14 to adjust generated stimulation pulses in accordance with the flow diagram in FIG. 4. The amplitude ramping capability shown in FIG. 4 provides mechanisms for selecting a target or goal amplitude, and then automates the intervening programming steps. The target amplitude can be set via the selection of the desired value from an on-screen list, the use of on-screen up and down arrow controls, and the use of a scroll wheel on the side of the device. The scroll wheel allows the iterative programming process to be accomplished one-handed, leaving the second hand free for the clinician to interact with the patient (to hold or squeeze their hand, for instance) in the OR setting. For those therapies with slower reaction times (MvD), the programmer 30 allows the use to configure the time between the automated programming steps.

Feedback of the ramping process is provided through the on-screen on user interface 305, as are mechanisms for stopping the ramp procedure (large stop-sign button corresponding to field 603 in FIG. 6), skipping directly to the target amplitude ("Program" button corresponding to field 605 in FIG. 6), and resetting the amplitude to zero volts (down arrow/rewind button corresponding to field 607 in FIG. 6) as will be discussed in the context of FIGS. 5-8.

The objective of a process 400 is for the clinician to determine the "best" specified parameter setting of stimulation pulses for the patient. For example, with pain therapy the "best" setting corresponds to reducing the patient's pain. In the embodiment, the specified parameter corresponds to an amplitude of the stimulation pulses. The clinician can also determine other settings such as a pulse rate (i.e. the frequency of the stimulation pulses). However, the embodiment of the invention facilitates the determination of the "best" setting for the pulse amplitude. Alternative embodiments may facilitate the determination of other specified parameters such as the pulse width of the stimulation pulses or the pulse rate of the stimulation pulses. With the automated process 400, the clinician does not need to manipulate the programmer 30 by executing keystrokes through the user interface 305 for each iteration of ramping the pulse amplitude, thus facilitating the adjustment process. When the patient indicates that the setting is "best," the patient notifies the clinician. Consequently, the ramping can be stopped in step 427 by the clinician terminating the process 400.

The ramping begins in step 401. In step 403, the current value of the pulse amplitude is compared to the target setting. If the target setting is less than the current value, step 411 is executed in which the current value is directly adjusted to the target setting, If the target setting is greater than the current value, the amplitude of stimulation pulses is increased by an incremental value in step 409. Step 409 corresponds to the processor 301 sending a command to the device 14 to increment the pulse amplitude between the designated electrode pair. However, the incremental setting of the amplitude may require that some of the parameters (e.g. a maximum limit) be modified as determined by steps 405 and 407.

With the incremental setting of the pulse amplitude in step 409, steps 413, 428, 415,417, and 419 are executed in order to determine whether an additional adjustment of the pulse amplitude is necessary. If the current value equals the target value in step 413, the ramping process is terminated. In step 428, if the clinician halts the ramping of the amplitude (through the user interface by selecting a field 603 in FIG. 6), and in step 429 the ramping of the amplitude stops, thus setting the amplitude to the current level. In step 415, if the clinician sets the amplitude to zero volts (through the user interface 305 by selecting a field 607 as shown in FIG. 6), possibly because the patient has discomfort, the pulse amplitude is set to zero in step 421 and the process 400 is halted. In step 417, the process 400 determines if the clinician wishes to set the current pulse amplitude directly to the target value (through the user interface by selecting field 605 in FIG. 6). If so, step 423 is executed and the ramping process 400 is terminated. In step 419, if a time delay between incremental settings of the pulse amplitude is greater than zero, the process 400 waits for the predetermined delay in step 425 before executing step 403, thus causing another iteration of the ramping process 400.

FIGS. 5, 6, 7, and 8 show exemplary screens that are displayed on the user interface 305 to support the amplitude ramping process 400.

FIG. 5 shows a programming tab with amplitude ramp control screen 500 that is displayed on the user interface 305 in accordance with an embodiment of the present invention. A status bar 501 indicates the status of the programmer 30. Examples of the status include a communications module status, a printer status, and a battery status. A title bar 503 comprises a device type (corresponding to the device 14), a mode of operation (e.g. demo mode), and a screen name. A screen tabs field 505 allows the clinician to select a patient profile screen, quick look, screen, programming screen, special screen, or data screen. A field 507 activates or deactivates the implanted device 14. In FIG. 5, the programming screen is selected. In a field 509, the clinician selects a lead that is associated with the device 14 if there is a plurality of leads. A field 511 shows the current pulse amplitude and the target pulse amplitude. Fields 513 and 515 increment and decrement the target pulse amplitude, respectively. Fields 519 and 521 show the current values of the pulse width and the pulse rate of the stimulation pulses, respectively. A field 523 controls electrode programming. An image 525 represents the lead 12 that is being programmed with the associated electrodes. With this example, lead 12 contains 4 electrodes (0, 1, 2, and 3). Electrodes 3 (a field 527) and 0 (a field 529) are selected with positive and negative polarities, respectively. The clinician can select the electrodes by touching the appropriate portions of the screen 500 or can manipulate fields 531 and 533 to select the electrodes.

FIG. 6 shows a ramp in progress screen 600 that is displayed on the user interface 305. A field 601 shows the current value of the pulse amplitude (0.3 volts) while being incremented to a target value of 4.5 volts. The clinician can halt the ramping process 400 by touching field 603 (as discussed in the context of step 428). The clinician can set the pulse amplitude to zero by selecting field 607 (as discussed in the context of step 415). Also, the clinician can set the current setting to the target setting by selecting field 605 (as discussed in the context of step 417).

FIG. 7 shows an amplitude and ramp time step selection screen 700 that is displayed on the user interface 305. An area 701 enables the clinician to select a target amplitude for the stimulation pulses. An area 703 enables the clinician to select the incremental step size between iterations of the process 400. An area 705 enables the clinician to select a time delay between iterations of the process 400.

FIG. 8 shows a completing a ramp screen 800 that is displayed in the user interface. An area 801 shows the status of the process 400. In FIG. 8, the area 801 indicates that the programmer 30 is communicating with the device 14 over the communications channel (telemetry channel).

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Thus, embodiments of the AMPLITUDE RAMPING OF WAVEFORMS GENERATED BY AN IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for adjusting a specified parameter associated with a stimulation pulse, the stimulation pulse generated by an implanted medical device, the method comprising:
   receiving user input that sets an incremental value of the specified parameter via a user interface of an external device that communicates with the implanted medical device;
   receiving user input that sets a target value of the specified parameter via the user interface of the external device;
   in response to the user input that sets the target value, automatically increasing a current value of the specified parameter by the incremental value a plurality of times, wherein automatically increasing a current value of the specified parameter by the incremental value a plurality of times comprises automatically sending a plurality of commands from an external programmer to the implantable medical device, each of the commands increasing the current value of the specified parameter by the incremental value;
   receiving a request to terminate the automatic increasing of the current value of the specified parameter; and
   terminating the automatic increasing of the current value of the specified parameter, wherein a final value of the specified parameter equals the current value of the specified parameter.

2. The method of claim 1, wherein the specified parameter characterizes an amplitude of the stimulation pulse between a pair of electrodes that is associated with the implanted device.

3. A method for adjusting a specified parameter associated with a stimulation pulse, the stimulation pulse generated by an implanted medical device, the method comprising the steps of:
   (a) initializing a current value of the specified parameter associated with the stimulation pulse;
   (b) determining an incremental value of the specified parameter;
   (c) automatically increasing the current value of the specified parameter in response to step (b); and
   (d) setting the current value of the specified parameter to a final value, wherein the step of setting comprises the steps of:
      (i) receiving a request to skip to a target value; and
      (ii) setting the current value to the target value.

4. A method for adjusting a specified parameter associated with a stimulation pulse, the stimulation pulse generated by an implanted medical device, the method comprising:
   receiving user input that sets a target value of the specified parameter via a user interface of an external device that communicates with the implanted medical device;
   in response to the user input that sets the target value, automatically increasing a current value of the specified parameter by a predetermined incremental value a plurality of times based on a comparison of the current value to the target value;
   during the automatic increasing of the current value and prior to the current value reaching the target value, receiving a request to halt the automatic increasing of the current value of the specified parameter;
   halting the automatic increasing of the current value of the specified parameter in response to the request; and
   identifying the current value of the specified parameter when the automatic increasing is halted as a final value.

5. A method for adjusting an amplitude associated with a stimulation pulse, the stimulation pulse generated by an implanted medical device, the method comprising:
   receiving user input that sets a target value of the amplitude via a user interface of an external device that communicates with the implanted medical device;
   in response to the user input that sets the target value, automatically increasing a current value of the amplitude by a predetermined incremental value a plurality of times based on a comparison of the current value to the target value;
   during the automatic increasing, determining whether to modify a value of another parameter associated with the stimulation pulse based on a next value of the amplitude that is the current value increased by the predetermined incremental value; and modifying the other parameter based on the determination.

6. Apparatus for adjusting a specified parameter of a stimulation pulse between a pair of electrodes that is associated with an implanted device, the apparatus comprising:

a user interface;

a communications module; and a processor that communicates with the implanted device through the communications module, the processor configured to:

receive user input that sets a target value of the specified parameter via the user interface;

in response to the user input that sets the target value, automatically increment a current value of the specified parameter by a predetermined incremental value a plurality of times based on a comparison of the current value to the target value;

during the automatic incrementing of the current value and prior to the current value reaching the target value, receive a request to halt the automatic incrementing of the current value of the specified parameter;

halt the automatic incrementing of the current value of the specified parameter in response to the request; and identify the current value of the specified parameter when the automatic incrementing is halted as a final value.

7. The apparatus of claim 6, wherein the processor is configured to accept oral instructions.

8. External apparatus for adjusting a specified parameter of a stimulation pulse between electrodes that are associated with an implanted medical device, the apparatus comprising:

a user interface;

a communications module; and a processor that communicates with the implanted device through the communications module, the processor configured to:

receive user input that sets an incremental value of the specified parameter via the user interface;

receive user input that sets a target value of the specified parameter via the user interface;

in response to the user input that sets the target value, automatically send a plurality of commands to the implantable medical device, each of the commands increasing the current value of the specified parameter by the incremental value, in order to automatically increase the current value of the specified parameter by the incremental value a plurality of times;

receive a request to terminate the automatic increasing of the current value of the specified parameter; and terminate the automatic increasing of the current value of the specified parameter, wherein a final value of the specified parameter equals the current value of the specified parameter.

9. A computer-readable medium containing instructions for controlling an external computer system to adjust a specified parameter of a stimulation pulse between electrodes that are associated with an implanted device by:

receiving user input that sets an incremental value of the specified parameter via a user interface of an external device that communicates with the implanted medical device;

receiving user input that sets a target value of the specified parameter via the user interface of the external device;

in response to the user input that sets the target value, automatically increasing a current value of the specified parameter by the incremental value a plurality of times, wherein automatically increasing a current value of the specified parameter by the incremental value a plurality of times comprises automatically sending a plurality of commands to the implantable medical device, each of the commands increasing the current value of the specified parameter by the incremental value;

receiving a request to terminate the automatic increasing of the current value of the specified parameter; and terminating the automatic increasing of the current value of the specified parameter, wherein a final value of the specified parameter equals the current value of the specified parameter.

* * * * *